United States Patent
Wilson (10) Patent No.: US 7,422,580 B2
(45) Date of Patent: Sep. 9, 2008

(54) METHOD FOR GUIDE CATHETER POSITIONING

(75) Inventor: Bruce Wilson, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 235 days.

(21) Appl. No.: 11/027,090

(22) Filed: Dec. 30, 2004

(65) Prior Publication Data

US 2005/0187534 A1  Aug. 25, 2005

Related U.S. Application Data

(62) Division of application No. 10/774,051, filed on Feb. 6, 2004, now Pat. No. 7,267,663.

(51) Int. Cl.
*A61M 31/00* (2006.01)
*A61M 37/00* (2006.01)
*A61M 25/00* (2006.01)

(52) U.S. Cl. ............... 604/510; 604/95.01; 604/528

(58) Field of Classification Search ... 604/95.01–96.01, 604/528, 510, 40–43, 117
See application file for complete search history.

(56) References Cited

U.S. PATENT DOCUMENTS

| | | | |
|---|---|---|---|
| 4,757,827 A | 7/1988 | Buchbinder et al. | |
| 5,334,187 A | 8/1994 | Fischell et al. | |
| 5,396,880 A * | 3/1995 | Kagan et al. | 600/109 |
| 5,454,827 A * | 10/1995 | Aust et al. | 606/170 |
| 5,545,200 A * | 8/1996 | West et al. | 607/122 |
| 5,827,313 A * | 10/1998 | Ream | 606/171 |
| 5,876,373 A * | 3/1999 | Giba et al. | 604/95.04 |
| 5,938,616 A * | 8/1999 | Eaton et al. | 600/463 |
| 5,957,941 A * | 9/1999 | Ream | 606/159 |
| 6,179,809 B1 * | 1/2001 | Khairkhahan et al. | 604/95.04 |
| 6,409,672 B2 * | 6/2002 | Webler et al. | 600/463 |
| 6,416,511 B1 | 7/2002 | Lesh et al. | |
| 6,554,794 B1 * | 4/2003 | Mueller et al. | 604/95.04 |
| 6,706,018 B2 * | 3/2004 | Westlund et al. | 604/194 |
| 6,726,675 B1 * | 4/2004 | Beyar | 604/510 |
| 6,755,812 B2 * | 6/2004 | Peterson et al. | 604/528 |
| 7,267,663 B2 * | 9/2007 | Wilson | 604/95.01 |
| 2002/0087048 A1 * | 7/2002 | Brock et al. | 600/114 |
| 2003/0120295 A1 | 6/2003 | Simpson et al. | |

* cited by examiner

*Primary Examiner*—Kevin C. Sirmons
*Assistant Examiner*—Andrew M Gilbert
(74) *Attorney, Agent, or Firm*—Hollingsworth & Funk, LLC (57) ABSTRACT

A method of catheter manipulation involves providing a catheter comprising a flexible shaft having a distal end shaped for accessing a target vessel. The method further involves selectably moving the shaft between a plurality of discrete positions of a first degree-of-freedom defined relative to the flexible shaft, restraining a motion of the shaft in the first degree-of-freedom at each position of the plurality of discrete positions, and moving the flexible shaft through a second degree-of-freedom defined relative to the flexible shaft at each position of the plurality of discrete positions. Moving the flexible shaft through the second degree-of-freedom results in a controllable sweeping motion at the distal end of the flexible shaft.

14 Claims, 6 Drawing Sheets

METHOD FOR GUIDE CATHETER POSITIONING

RELATED PATENT DOCUMENTS

This is a divisional of U.S. Pat. application Ser. No. 10/774,051, filed on Feb. 6, 2004, now U.S. Pat. No. 7,267,663, issued on Sep. 11, 2007, to which Applicant claims priority under 35 U.S.C. §120, and which is incorporated herein by reference.

FIELD OF THE INVENTION

The invention relates generally to catheterization and catheter systems, and, more particularly, to a method for positioning guide catheters.

BACKGROUND

Guiding catheters are indispensable medical devices that allow a physician to locate and cannulate vessels in a patient's anatomy for performing various medical procedures. Guiding catheters are commonly used in cardiac access procedures such as heart vessel mapping (venography) and implanting of cardiac pacing devices. Cannulating heart vessels typically requires navigating a small diameter, flexible guide through convoluted vasculature into a heart chamber, and then into a destination heart vessel. Once the destination heart vessel is reached, the catheter acts as a conduit for insertion of payloads into the vessel.

In one example of a cardiac implant procedure, pacing devices may be implanted on both sides of the heart. One pacing device is placed in the right ventricle and the other pacing device is placed in the great coronary vein. A guiding catheter can be used to implant this second device into the coronary vein by cannulating the coronary sinus ostium (located in the right atrium) with the catheter.

The ostium of the coronary sinus is a relatively small opening in the right atrium that provides access to the coronary sinus. As a result, the procedure involved in locating the ostium can be time consuming and difficult. The physician may have various aids in locating the coronary sinus, such as imaging or sensors. Notwithstanding such aids, locating the ostium can still be hit or miss, as it relies on the skill of the physician in properly manipulating the proximal end of the catheter. A more organized way of allowing the physician to search for a vessel such as the coronary sinus is desirable.

SUMMARY

The present disclosure describes a method for guided catheterization. According to an embodiment of the present invention, a method of catheter manipulation involves providing a catheter comprising a flexible shaft having a distal end shaped for accessing a target vessel. The method further involves selectably moving the shaft between a plurality of discrete positions of a first degree-of-freedom defined relative to the flexible shaft, restraining a motion of the shaft in the first degree-of-freedom at each position of the plurality of discrete positions, and moving the flexible shaft through a second degree-of-freedom defined relative to the flexible shaft at each position of the plurality of discrete positions. Moving the flexible shaft through the second degree-of-freedom results in a controllable sweeping motion at the distal end of the flexible shaft.

In accordance with another embodiment, a method of catheter manipulation involves introducing a catheter shaft into an access vessel that provides access to a destination vessel. The method further involves repeatedly performing, until the destination vessel is located by a distal end of the catheter shaft, steps comprising: mechanically restraining a proximal end of the catheter shaft from travel in a first degree-of-freedom relative to the catheter shaft at one of a plurality of positions of the first degree-of-freedom; moving the proximal end of the catheter shaft through a mechanically limited displacement of a second degree-of-freedom defined relative to a centerline of the catheter shaft; and cannulating the destination vessel with the distal end of the catheter shaft.

In one aspect of a catheter manipulation method, a first degree-of-freedom includes a longitudinal displacement relative to the flexible shaft, and a second degree-of-freedom includes an axial rotation relative to the flexible shaft. In another aspect, a first degree-of-freedom includes an axial rotation relative to the flexible shaft, and a second degree-of-freedom includes a longitudinal displacement relative to the flexible shaft. Methods may also involve moving the shaft through mechanically limited displacement via a handle assembly movably coupled to the catheter shaft. Methods may further involve adjustably locating the handle assembly on the proximal end of the catheter shaft.

In a further embodiment, a guiding catheter system includes a flexible shaft having a distal end shaped for accessing a target vessel. A handle assembly is movably coupled to the flexible shaft. The flexible shaft is selectably movable between a plurality of discrete positions of a first degree-of-freedom defined relative to the flexible shaft. The flexible shaft restrained in the first degree-of-freedom at each position of the plurality of discrete positions. The flexible shaft movable through a predetermined displacement of a second degree-of-freedom defined relative to the flexible shaft at each position of the plurality of discrete positions. Motion of the flexible shaft relative to the handle assembly results in a controllable sweeping motion at the distal end of the flexible shaft.

In one arrangement, the first degree-of-freedom includes a longitudinal displacement relative to the flexible shaft, and the second degree-of-freedom includes an axial rotation relative to the flexible shaft. In another arrangement, the first degree-of-freedom includes an axial rotation relative to the flexible shaft, and the second degree-of-freedom includes a longitudinal displacement relative to the flexible shaft. The handle assembly may include a guide member attached to the shaft, and a housing movable coupled to the guide member via a slot and pin arrangement. The handle assembly may include a tightening member between the flexible shaft and the handle assembly, the tightening member providing a releasable coupling between the flexible shaft and the handle assembly

DETAILED DESCRIPTION

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

In broad and general terms, the present invention is directed to methods for guide catheterization that are suitable for placing devices in anatomical locations such as cardiac vessels. In one embodiment, the catheter includes an improved guide handle to assist in a methodical and thorough search for an anatomical feature at the catheter's distal end.

Figure 1:
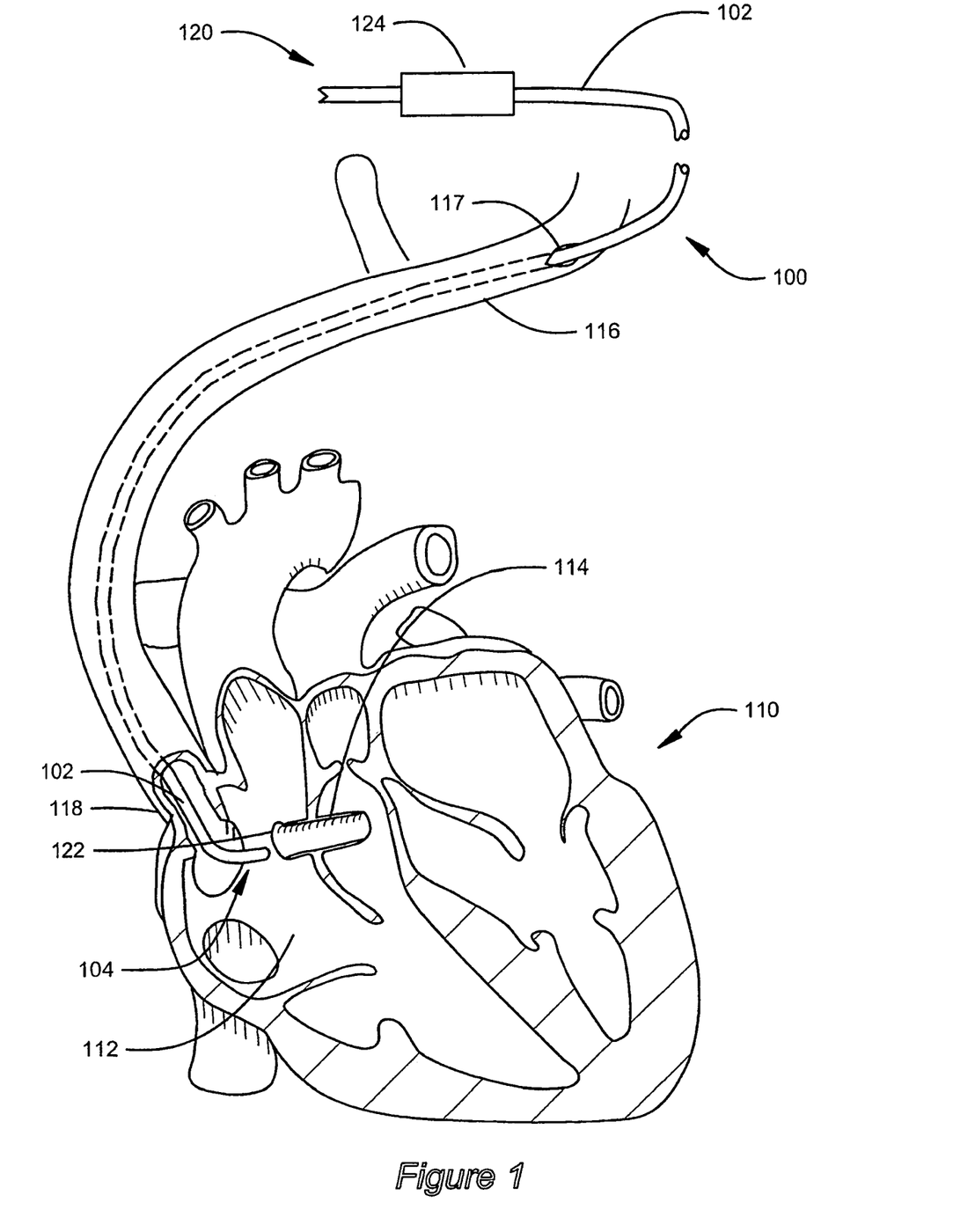
FIG. 1 is a cutaway view of a heart showing a guiding catheter according to embodiments of the present invention positioned in the right atrium.

With reference to FIG. 1, a guiding catheter assembly 100 is illustrated according to embodiments of the present invention. The guiding catheter assembly 100 includes an elongated, flexible shaft 102 that can be introduced in anatomical passageways to support medical procedures. The medical procedures may include delivery of drugs, sensors, pacing leads, defibrillation leads, or other diagnostic objects into the heart 110 and associated vessels.

The flexible shaft 102 may be formed of an extruded tube of a single polymer material. Alternatively, the shaft 102 may be assembled using a multiple-layer construction. Typically, multi-layer shafts include a core tubing portion with various coatings/layers on inner and outer surfaces to impart desired properties to those surfaces while still keeping the shaft reasonably flexible. Typically, outer surface coatings are chosen to provide an impermeable and smooth outer surface, while inner surfaces may include lubricous coatings that allow easier movement of devices within the lumens. Other features may be included with the shaft 102, such as an embedded stainless steel or fiber braid, which provides longitudinal stiffness.

The flexible shaft 102 includes a pre-shaped distal end 104 that may be introduced into the target vessel. In this example, the distal end 104 is shown located in the right atrium 112 of the heart 110. The distal end 104 is shaped to access a particular target vessel. The target vessel may include heart vessels such as the coronary sinus 114. The coronary sinus 114 is often approached via an access vessel 116 of the vasculature such as the cephalic vein. An incision 117 is made in an access vessel 116 and the catheter assembly 100 introduced into the heart 110 from the incision 117. In the illustrated access path, the catheter enters the heart 110 through the superior vena cava 118 and into the right atrium 112.

While maneuvering the flexible shaft 102 to its destination, the distal end 104 may be placed in the general vicinity of the target vessel 114. The physician must carefully move a proximal end 120 of the flexible shaft 102 to locate the distal end 104 in an opening 122 of the target vessel 114. In this example, the opening includes the coronary sinus ostium 122. The physician may be assisted in locating the ostium 122 using visualization techniques such as X-ray fluoroscopy, and/or be assisted by sensors placed on the catheter shaft 102.

Even with visual and/or sensory aids, placing the distal end 104 of the catheter 100 into the ostium 122 can be difficult. The physician is manipulating a long and relatively flexible shaft 102 from the shaft's proximal end 120 while the shaft 102 is located in a tortuous venous pathway. This may result in exaggerated and uncontrolled movements (e.g., "whipping") at the proximal end 120. The flexible shaft 102 may offer little or no tactile feedback to the physician. This makes it difficult for the physician to perform a systematic probing of a particular area to locate the target vessel 114 or other anatomical feature.

To overcome these difficulties, the catheter 100 includes a handle 124 adapted to aid the physician in performing a systematic search for anatomical features at the distal end 104. Relative movement between the flexible shaft 102 and handle 124 is controlled in such a way that the physician can perform a systematic search for an anatomical feature at the catheter's distal end 104. The handle 100 includes features that provide more controlled movement at the shaft's distal end 104, as well as providing indexing features that allow the physician to perform the search in a methodical and repeatable fashion.

Figure 2:
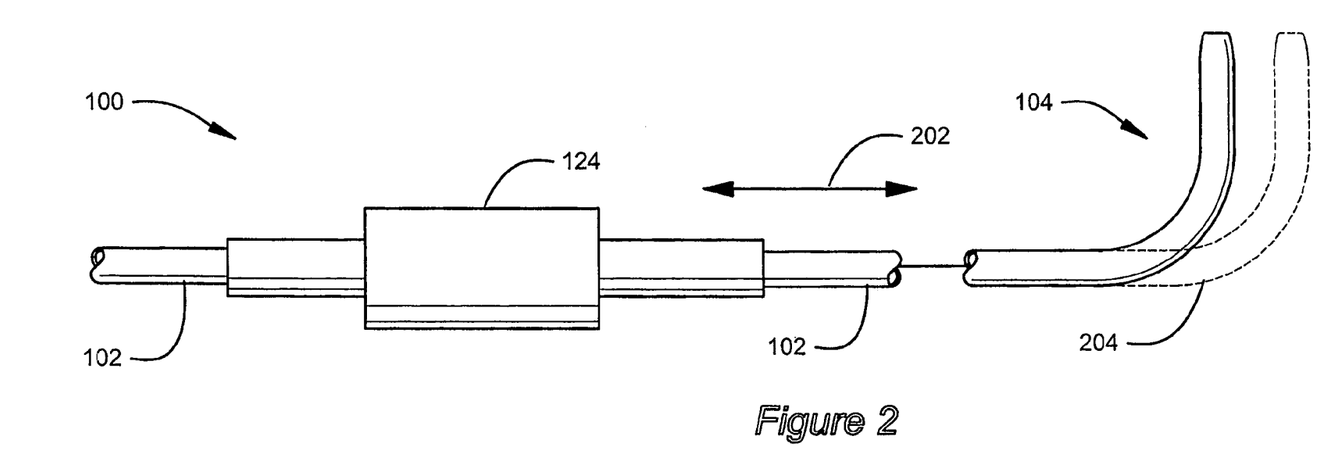
FIG. 2 is a side view of a guiding catheter handle showing relative longitudinal motion of the catheter shaft according to embodiments of the present invention.

In general, the handle 124 and shaft 102 may be relatively moveable both in longitudinal translation and axial rotation. The movements of the handle 124 and shaft 102 can be controlled in the translational and rotational directions to assist in a systematic search. In reference now to FIG. 2, a side view of the catheter 100 shows relative translational motion between the catheter handle 124 and shaft according to embodiments of the present invention. The shaft 102 can move in through all or part of the handle 124 in a longitudinal direction as indicated by the arrow 202. The effect of longitudinal motion is to displace the distal end 104 as indicated by the displaced end 204 drawn in broken lines.

Figure 3:
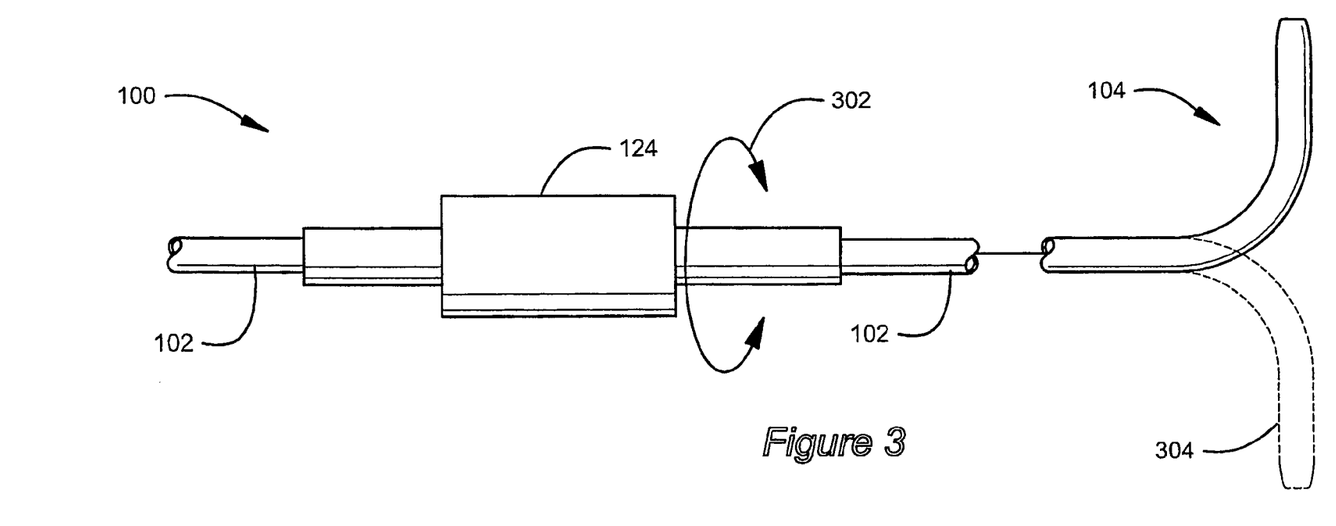
FIG. 3 is a side view of a guiding catheter handle showing relative axial rotation of the catheter shaft according to embodiments of the present invention.

In FIG. 3, a side view of the catheter 100 shows relative rotation between the catheter handle 124 and shaft according to embodiments of the present invention. The shaft 102 may be rotated along its longitudinal axis relative to all or part of the handle 124 as indicated by the curved arrow 302. The effect of longitudinal motion is to rotate the distal end 104, as indicated by the rotated position 304 shown in broken lines.

Figure 4:
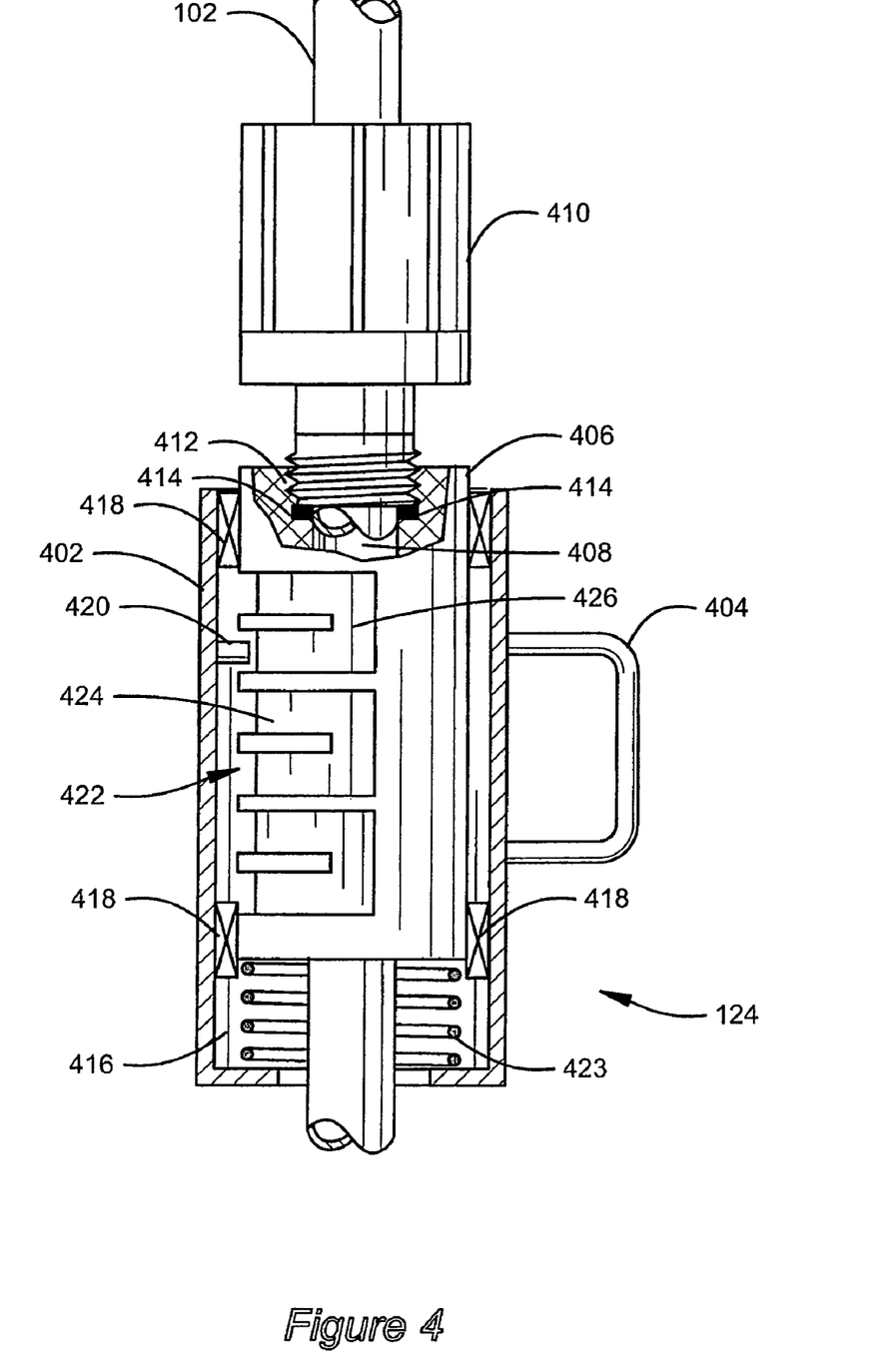
FIG. 4 is a cross-sectional view of the guiding catheter handle according to embodiments of the present invention.

It will be appreciated that the physician can longitudinally and rotationally move the shaft 102 without the use of the handle 124. The handle 124, however, provides a restraint on this motion, thereby allowing such movements to be systematic and controllable. One arrangement of a handle 124 and shaft 102 for enhanced shaft control according to embodiments of the present invention is shown in FIG. 4. The handle 124 includes an outer housing 402 that can be gripped by the physician. The housing 402 may contain features that provide easier holding and manipulation, such as a textured outer surface and/or a thumb handle 404.

The flexible shaft 102 may be fixably attached to a guide member 406. The guide member 406 has an inner bore 408 through which the flexible shaft 102 can pass. A sealing cap 410 attaches to a threaded portion 412 of the bore 408. The sealing cap 410 can be made from a standard rotating hemostatic valve (RHV) cap. When the sealing cap 410 is tightened, the cap 410 attaches the flexible shaft 102 to the guide member 406.

A seal 414 (e.g., an RHV seal) may be located between the guide member 406 and the flexible shaft 102. The seal 414 may be compressed by tightening of the sealing cap 410 to create a fluid-impermeable seal between the guide member 406 and the flexible shaft 102. Once the sealing cap 410 is tightened, the flexible shaft 102 and guide member 406 can be moved as a single unit.

The guide member 406 is movable within a bore 416 of the housing 402. To provide a smooth and low-friction interface between the guide member 406 and bore 416, bearings 418 may be employed. The bearings 418 may be separate elements such as pressed-in bushings. In other configurations, the bearings 418 may be formed as one or more features of the bore 416.

The movement of the guide member 406 within the bore 416 may be controlled via the interactions of a pin 420 and slot 422 arrangement. As shown, the pin 420 extends from the inner surface of the bore 416 and the slot 422 is formed in the guide member 406. A spring 423 can provide a compressive or tensile force that keeps the pin 420 and slot 422 from unintentionally shifting positions. It will be appreciated that a reverse configuration, with the pin 420 extending from the guide member 406 and the slot 422 formed in the bore 416, will provide a similar result as the illustrated arrangement.

The slot 422 may be formed as a serpentine path that includes a plurality of circumferential channels 424. These circumferential channels 424 correspond to a rotational movement between the catheter shaft 102 and handle 124 at fixed longitudinal orientations. The circumferential channels 424 are joined by axial segments 426 that provide transitions between adjacent fixed longitudinal orientations of the catheter shaft 102 and handle 124.

Figure 5:
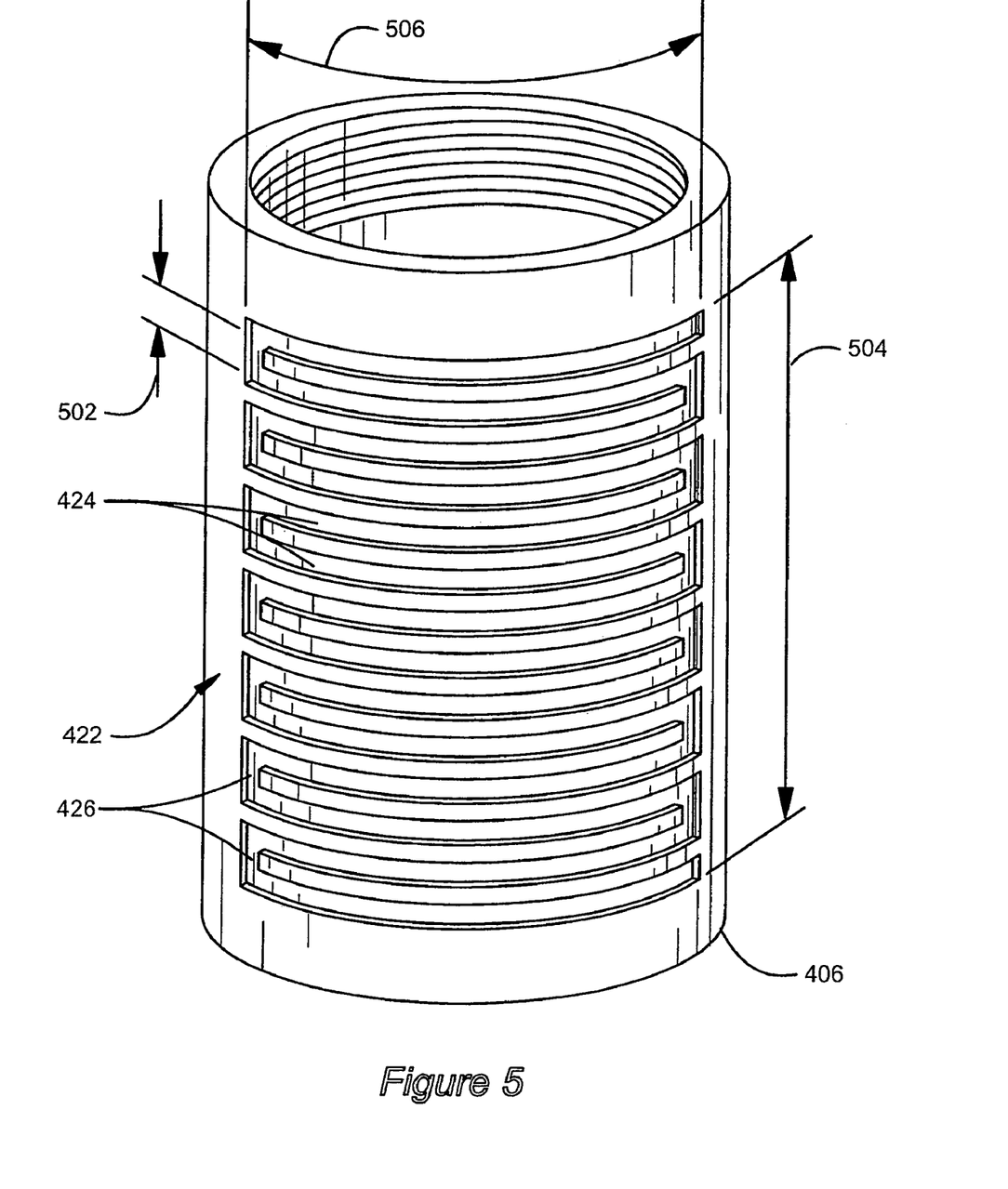
FIG. 5 is a perspective view of a slotted guide member according to embodiments of the present invention.

A perspective view of the slotted guide member 406 is shown in FIG. 5. The slot 422 includes circumferential channels 424 and axial segments 426 arranged on the outer surface of the guide member 406 in a serpentine configuration. A spacing distance 502 separates the circumferential channels 424. The spacing distance 502 may be a constant or variable distance between adjacent pairs of circumferential channels 424. The circumferential channels 424 each define a fixed longitudinal orientation within the total longitudinal travel length 504. In each fixed longitudinal orientation, the catheter shaft can rotate axially, but cannot move longitudinally relative to the handle.

The length of each circumferential channel 424 defines a rotation angle 506. The rotation angle 506 defines the maximum angle that the catheter shaft can be rotated for a given longitudinal location. The circumferential channels 424 may be of substantially identical length, so that the rotation angle 506 is the same at each longitudinal orientation. In other arrangements, the rotation angle 506 may be different at different longitudinal orientations. It will be appreciated that the movement of the guide member 406 may be adjustably limited to a lesser longitudinal travel length 504 and rotation angle 506 than provided by the slot arrangement 422. For example, an adjustable stop member may be placed between the guide member 406 and the housing 402 (see FIG. 4) to limit one or both of relative rotation and longitudinal travel.

The slot 422 configuration shown in FIG. 5 is only one possible configuration that can provide a catheter assembly with guiding features according to the present invention. For example, the axial segments 426 may be formed as curved segments that more smoothly join adjacent circumferential channels 424. In another configuration, the axial segments 426 may be joined into a single channel that extends across the entire longitudinal travel length 504, so that the slot arrangement 422 resembles a ladder.

Figure 6:
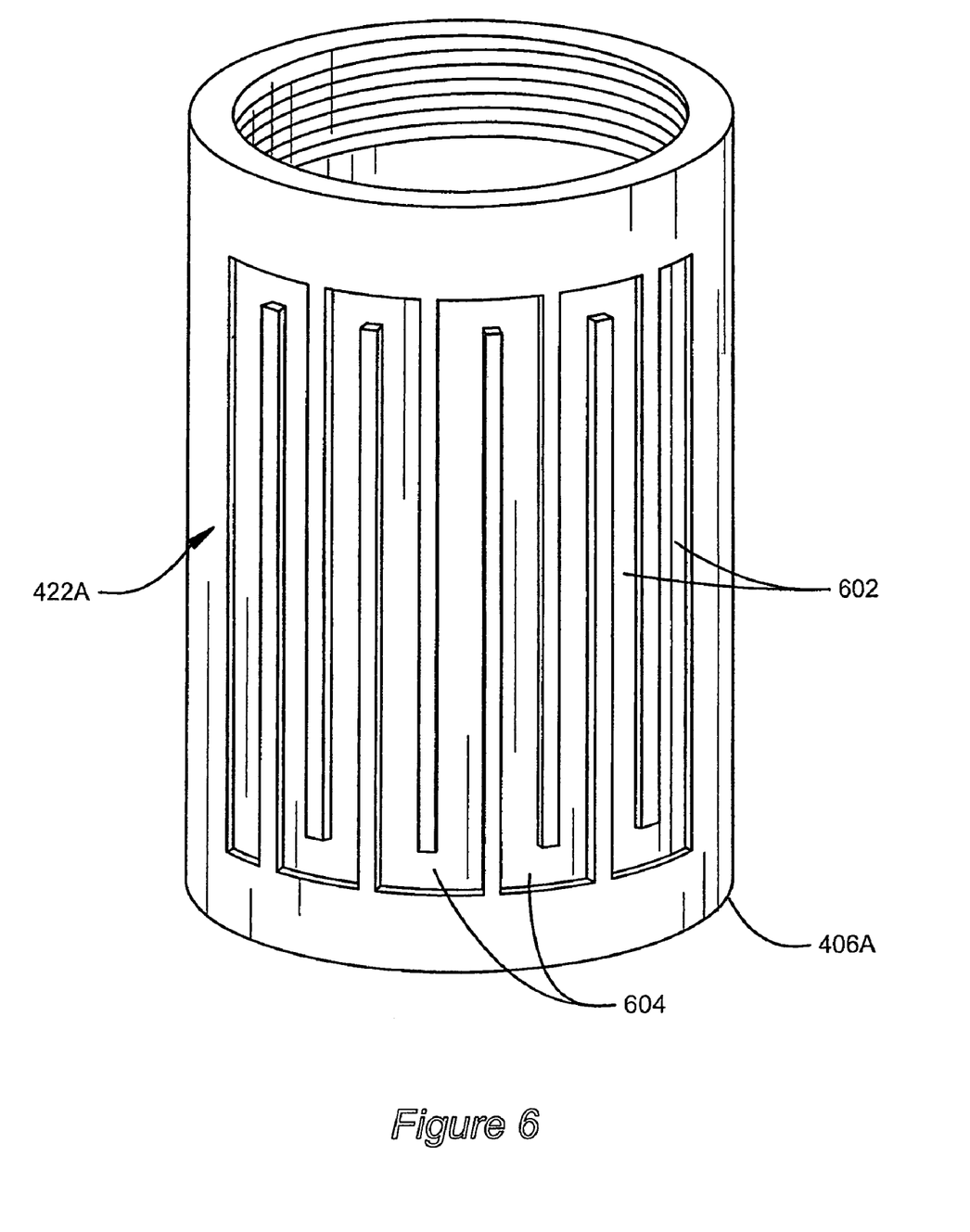
FIG. 6 is a perspective view of a slotted guide member with an alternate slot arrangement according to embodiments of the present invention.

In general, any slot arrangement that allows a user to perform a systematic traversal of a search area may be used with an apparatus as described herein. In general, the slot arrangement fixes the catheter shaft in discrete positions of a first degree-of-freedom while allowing the catheter to move though a displacement of a second degree-of-freedom. For example, FIG. 6 illustrates an alternate slot arrangement 422A for a guide member 406A of a catheter according to embodiments of the present invention. This slot arrangement 422A include a plurality of axial channels 602 that are joined by circumferential segments 604 to form a serpentine shape. In contrast to the slot 422 shown in FIG. 5, the slot 422A allows constant longitudinal translation at a plurality of fixed rotational angles. Each of the axial channels 602 corresponds to a fixed rotational angle.

Figure 7:
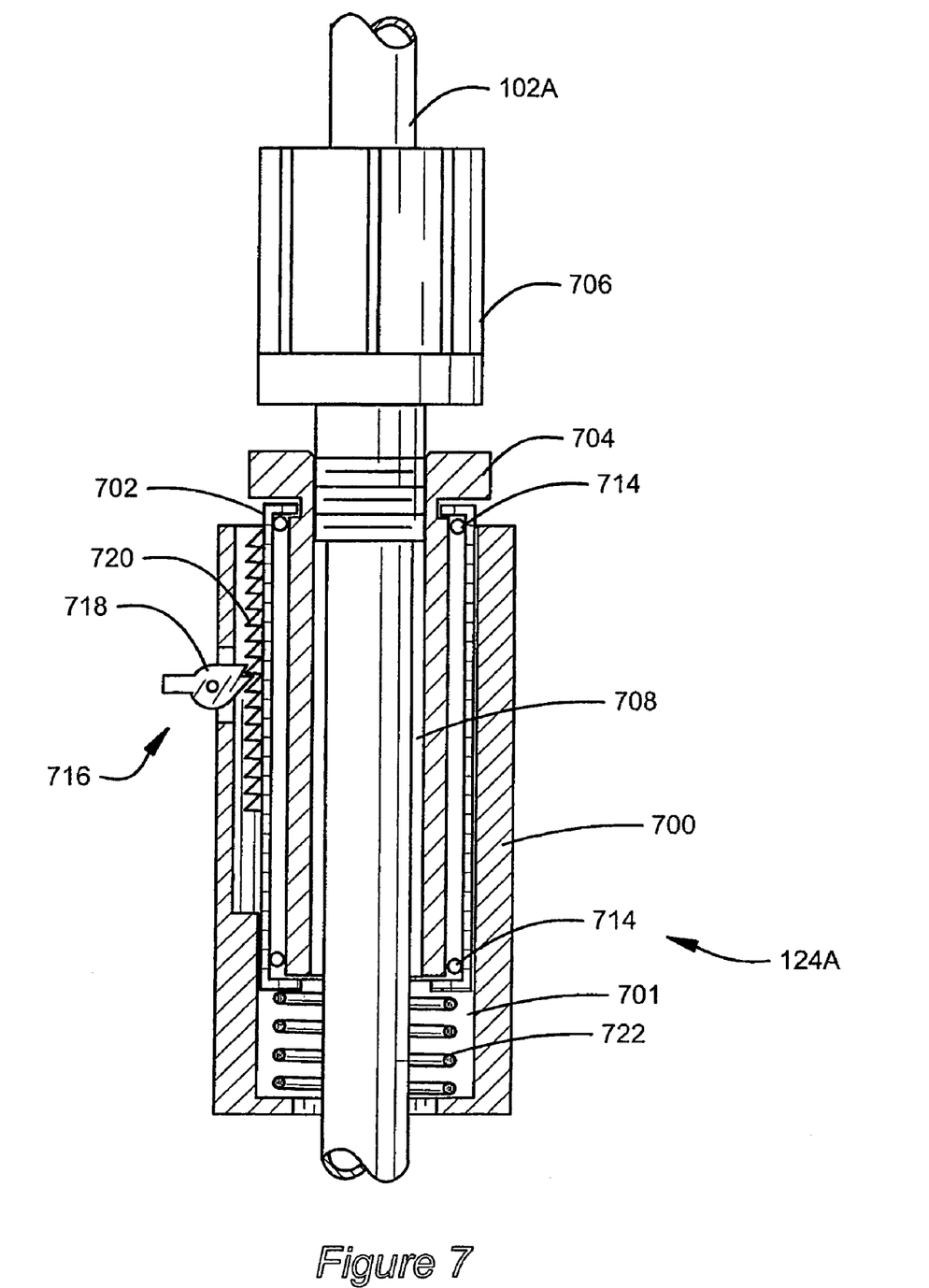
FIG. 7 is a cross-sectional view of an alternate arrangement of the guide handle according to embodiments of the present invention.

Mechanical apparatuses other than a pin-slot arrangement may be used to movably couple a catheter shaft and handle as described. FIG. 7 illustrates an alternate catheter handle assembly 124A that may be used with a catheter assembly according to embodiments of the present invention. The handle 124A includes an outer housing 700 that may be gripped by the user.

The outer housing 700 has a bore 701 in which a slide housing 702 is placed. A rotating member 704 is located within the slide housing 702. The rotating member 702 has an inner bore 708 through which the flexible shaft 102A can pass. The flexible shaft 102A can be fixably attached to the rotating member 704 using an RHV sealing cap 706 or similar apparatus.

The rotating member 704 can turn within the slide housing 702. One or more bearings 714 may be employed to provide a low-friction rotational interface between the rotating member 704 and the slide housing 702. The extent that the rotating member 704 may turn within the slide housing 702 may be limited to an angle analogous to the rotation angle 506 shown in FIG. 5. The rotation angle may be limited by features (not shown) on the rotating member 704 or slide housing 702. These rotational limits may be fixed or adjustable.

The slide housing 702 is longitudinally movable relative to the outer housing 700, and this motion is typically limited to discrete steps. A longitudinal indexing mechanism 716 may be used to provide discrete control of longitudinal motion between the slide housing 702 and the outer housing 700. The indexing mechanism 716 may include such features as a ratchet 718 and linear gear 720 for moving or indexing the slide housing 702 in discrete steps. Other mechanical features known in the art may be also used as an indexing mechanism 716, such as thumbwheels, ball and detent arrangements, frictional stops, etc. A spring 722 may be used provide a compressive or tensile force to assist the operation of the indexing mechanism 716.

Referring again to FIG. 1, the guiding catheter assembly 100 may be used in procedures that require anatomical access via a convoluted pathway. Guiding catheters are commonly utilized in heart treatments because of the indirect access routes used to enter the heart. In one example, provided for purposes of illustration, a congestive heart failure treatment may involve implanting a pacing lead into the coronary sinus 114. In some implantation procedures, the guiding catheter assembly 100 is introduced through an incision 117 in the upper vasculature. The catheter shaft 102 can be introduced through this incision and into a guide vessel 116 of the vasculature. The distal end 104 of the catheter shaft 102 enters into the right atrium 112 through the superior vena cava 118.

After the shaft's distal end 104 is located in the right atrium 112, the shaft 102 must be manipulated to place the shaft's distal end 104 in the coronary sinus 114. The ostium 122 of the coronary sinus 114 is located on a wall of the atrium 112 and the procedure typically requires considerable manipulation to place the catheter shaft 102 into the ostium 122. The shaft 102 may include a shaped distal end 104 specially designed for this task.

After the catheter shaft 102 is located in the atrium 112, the handle assembly 124 may be slid over a distal part of the flexible shaft 102 and tightened into place. It will be appreciated that the handle assembly 124 may be formed integrally with the catheter shaft 102, so that the handle assembly 124 is already located at a distal part of the shaft 102 during this part of the procedure. In either case, the physician may have the ability adjust the location of the handle assembly 124 relative to the shaft 102 to so that the handle assembly 124 is positioned for maximum control and comfort.

Once an optimum location of the handle assembly 124 is found, the handle assembly can be tightened on the shaft 102, such as by using an RHV seal cap 410 (see FIG. 4). Other adjustments may also be required before or after tightening the handle assembly 124, such as setting the appropriate rotational orientation and/or setting adjustable stops that control relative movement between the shaft 102 and handle assembly 124. The physician can then begin to move the shaft 102 within the handle assembly 124 to provide a sweeping motion at the shaft's distal end 104. The sweeping motion continues until the ostium 122 is located.

Other features known in the art may be included with the guiding catheter assembly 100 to assist in this search for the ostium 122. A steering apparatus (not shown) may be used in the catheter shaft 102 to allow deflection of the distal end 104 during access procedures. Such steering apparatuses typically include tensile members slidably deployed in lumens of the shaft 102 and fixed near the distal end 104 of the shaft. The tendons are pulled at the catheter assembly's proximal end 120 to change a bend angle of the distal end 104. During a sweeping search using the handle assembly 124, various bend angles may be set at the distal end by using a steering apparatus.

The catheter assembly 100 may also utilize sensors (not shown) mounted on the distal end 104 of the shaft 102. These sensors may include any combination of temperature, ultrasound, visual, pressure, velocity, conductivity, and/or fluid flow sensors, as well as electrodes (e.g., mapping electrodes). Outputs of the sensors can be monitored during the sweeping search for the ostium 122. By utilizing a handle assembly 124 for a smooth and controllable sweeping search, the output of such sensors will tend to be less erratic and therefore be more useful to assist in finding the ostium.

It will, of course, be understood that various modifications and additions can be made to the embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of catheter manipulation, comprising:
    providing a catheter comprising a flexible shaft having a distal end shaped for accessing a target vessel;
    moving the shaft between a plurality of first discrete indexing positions in a first degree-of-freedom defined relative to the flexible shaft while mechanically restraining a motion of the shaft in a second degree of freedom; and
    moving the shaft in the second degree-of-freedom defined relative to the shaft between a plurality of second discrete indexing positions while mechanically restraining a motion of the shaft in the first degree-of-freedom between each position of the plurality of second discrete indexing positions, wherein a handle assembly is coupled to a proximal end of the flexible shaft, and performing the selectably moving, restraining motion, and moving steps to the flexible shaft is facilitated by relative movement between a serpentine slot arrangement and a pin arrangement that moveably couple the flexible shaft and the handle assembly.

2. The method of claim 1, wherein moving the flexible shaft between the plurality of second discrete indexing positions results in a controllable sweeping motion at the distal end of the flexible shaft.

3. The method of claim 1, wherein the first degree-of-freedom comprises a longitudinal displacement relative to the flexible shaft, and the second degree-of-freedom comprises an axial rotation relative to the flexible shaft.

4. The method of claim 1, wherein the first degree-of-freedom comprises an axial rotation relative to the flexible shaft, and the second degree-of-freedom comprises a longitudinal displacement relative to the flexible shaft.

5. The method of claim 1, wherein restraining motion of the shaft in the first degree-of-freedom comprises restraining motion of a proximal end of the flexible shaft in the first degree-of-freedom.

6. The method of claim 1, wherein moving the flexible shaft through the second degree-of-freedom comprises moving a proximal end of the flexible shaft through the second degree-of-freedom.

7. The method of claim 1, further comprising:
    introducing the flexible shaft into an access vessel that provides access to the target vessel;
    performing the selectably moving, restraining motion, and moving steps to the flexible shaft for locating the target vessel; and
    cannulating the target vessel with the distal end of the flexible shaft.

8. The method of claim 7, further comprising delivering a payload through the flexible shaft and to the target vessel.

9. The method of claim 8, wherein the payload comprises one or more of a drug, a sensor, a pacing lead, and a defibrillation lead.

10. A method of catheter manipulation, comprising:
    introducing a catheter shaft into an access vessel that provides access to a destination vessel;
    repeatedly performing, until the destination vessel is located by a distal end of the catheter shaft, steps comprising:
        mechanically restraining a proximal end of the catheter shaft from travel in a first degree-of-freedom relative to the catheter shaft while moving the proximal end of the catheter shaft through a mechanically limited displacement of a second degree-of-freedom defined relative to a centerline of the catheter shaft to one of a plurality of discrete indexing positions; and
        moving the proximal end of the catheter shaft through a mechanically limited displacement of the first degree-of-freedom while mechanically restraining the proximal end of the catheter from travel in the second degree-of-freedom to another one of the plurality of discrete indexing positions; and
    cannulating the destination vessel with the distal end of the catheter shaft, wherein a handle assembly is coupled to the proximal end of the catheter shaft, and performing the moving and restraining steps is facilitated by relative movement between a serpentine slot arrangement and a pin arrangement that moveably couple the catheter shaft and the handle assembly.

11. The method of claim 10, wherein the first degree-of-freedom comprises a longitudinal displacement relative to a centerline of the flexible shaft, and the second degree-of-freedom comprises an axial rotation relative to the centerline of the flexible shaft.

12. The method of claim 10, wherein the first degree-of-freedom comprises an axial rotation relative to a centerline of the flexible shaft, and the second degree-of-freedom comprises a longitudinal displacement relative to the centerline of the flexible shaft.

13. The method of claim 10, wherein moving the proximal end of the catheter shaft through the mechanically limited displacement of the second degree-of-freedom results in a controllable sweeping motion at the distal end of the catheter shaft.

14. The method of claim 10, further comprising delivering a payload through the catheter shaft and to the destination vessel.

\* \* \* \* \*